United States Patent [19]
Reiten

[11] Patent Number: 5,191,893
[45] Date of Patent: Mar. 9, 1993

[54] VOLUME VARIATION SENSOR AND METHOD FOR OBSTRUCTIVE SLEEP APNEA MONITORING

[75] Inventor: Denise M. Reiten, Champlin, Minn.

[73] Assignee: CNS, Inc., Chanhassen, Minn.

[21] Appl. No.: 884,853

[22] Filed: May 12, 1992

Related U.S. Application Data

[63] Continuation of Ser. No. 525,892, May 18, 1990, abandoned.

[51] Int. Cl.[5] .............................................. A61B 5/113
[52] U.S. Cl. ..................................... 128/721; 128/782
[58] Field of Search ............... 128/686, 687, 689, 694, 128/716, 721, 774, 782

[56] References Cited
U.S. PATENT DOCUMENTS

| | | | |
|---|---|---|---|
| 2,194,809 | 3/1940 | Powell, Jr. | 128/721 |
| 2,233,506 | 3/1941 | Azaretti | 128/721 |
| 3,368,550 | 2/1968 | Glascock | 128/30.2 |
| 3,481,327 | 12/1969 | Drennen | 128/30.2 |
| 4,373,534 | 2/1983 | Watson | 128/725 |
| 4,381,788 | 5/1983 | Douglas | 128/722 |
| 4,559,953 | 12/1985 | Wright et al. | 128/680 |
| 4,602,643 | 7/1986 | Dietz | 128/721 |
| 4,813,429 | 3/1989 | Muraki et al. | 128/736 |

Primary Examiner—Lee S. Cohen
Assistant Examiner—Kevin Pontius
Attorney, Agent, or Firm—Kinney & Lange

[57] ABSTRACT

A volume change sensor having an elongated tubular enclosure with a thin deformable wall having a conduit for connection to a pressure monitor, there being an elongated insert material within the tubular enclosure that is wider than it is thick at some locations formed from resiliently deformable open cell foam. An elastic belt against which the tubular enclosure is positioned is used to wrap it about a respirating subject undergoing corresponding changes to measure same.

7 Claims, 4 Drawing Sheets

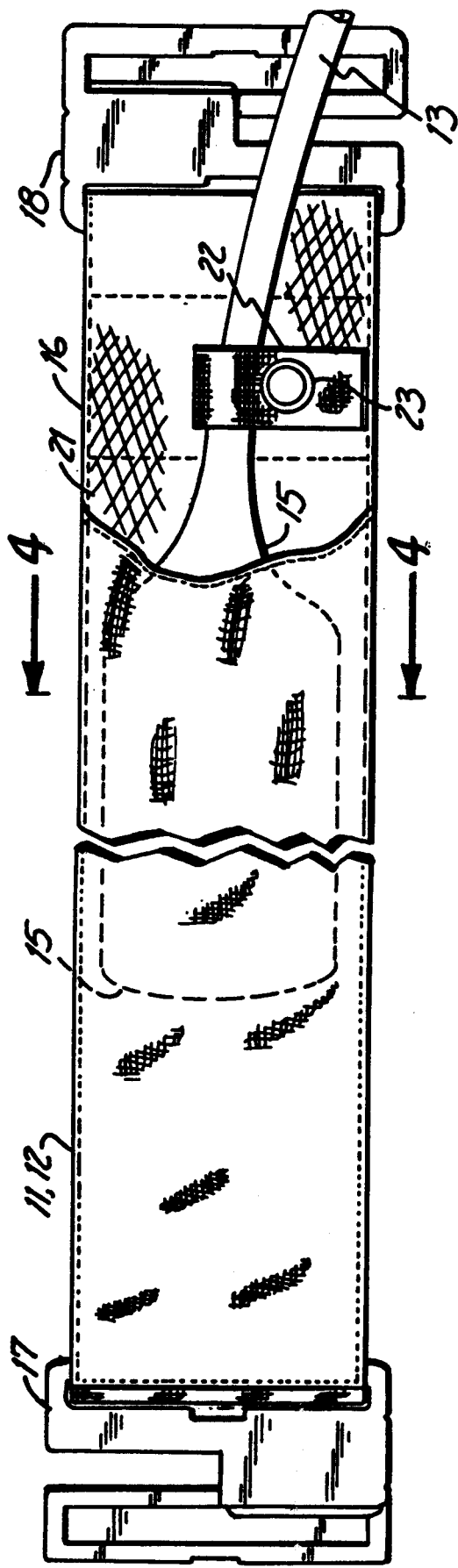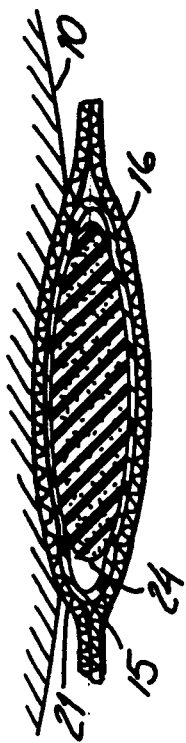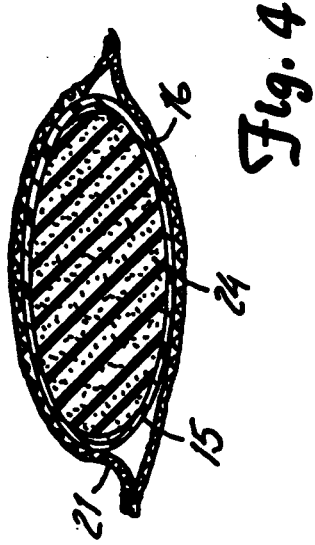

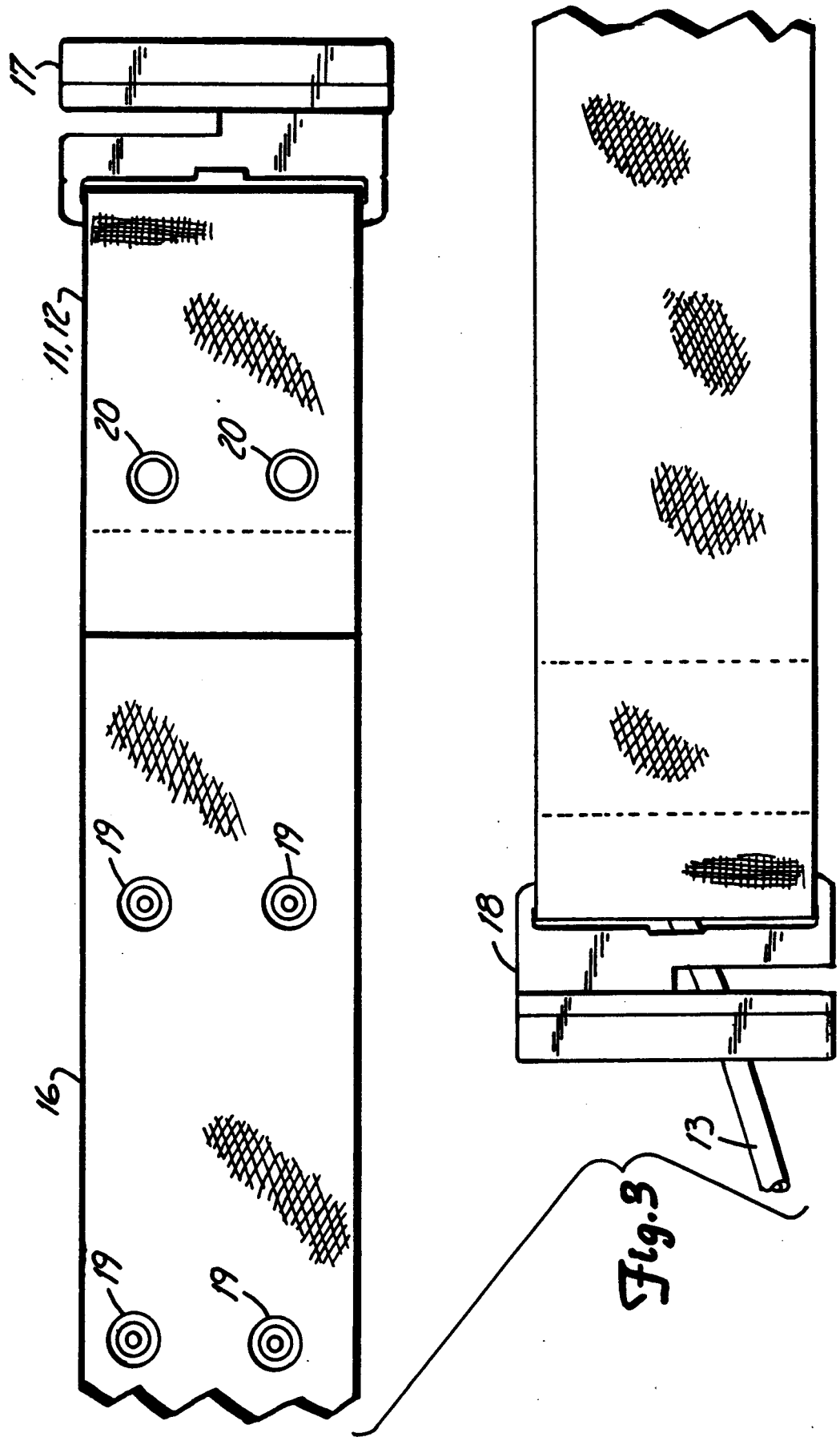

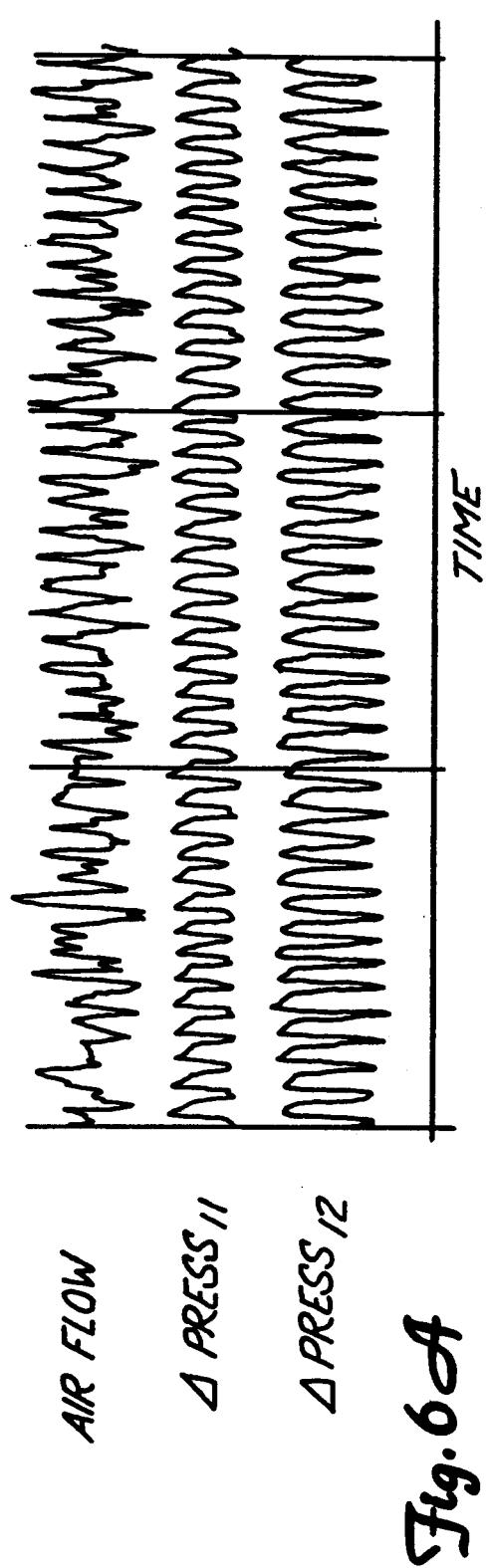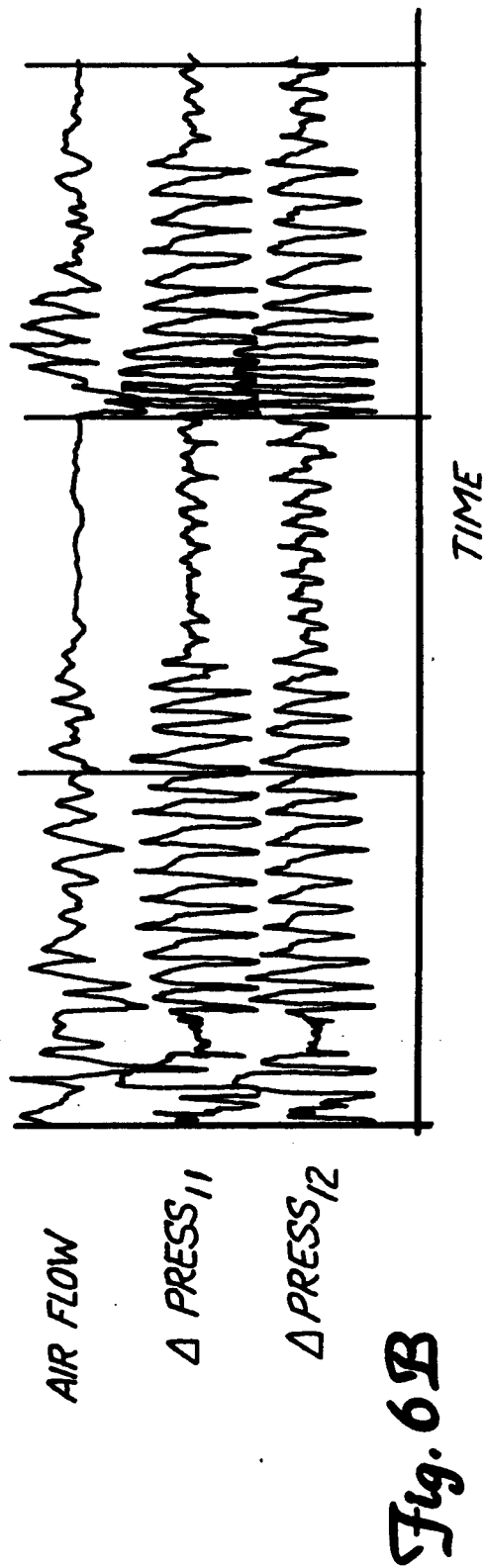

VOLUME VARIATION SENSOR AND METHOD FOR OBSTRUCTIVE SLEEP APNEA MONITORING

This is a continuation of application Ser. No. 07/525,892, filed May 18, 1990, now abandoned.

BACKGROUND OF THE INVENTION

The present invention relates to volume change monitors for use in detecting changes of a volume enclosed thereby which would typically be that of a section of a human torso and, more particularly, to determine volume changes during respiration as an indicator of the occurrence of apneas in the human being monitored.

As is becoming increasingly recognized, interference with sleep in humans due to irregularities in bodily systems is emerging as a causative factor in an increasing number of human maladies. A corollary of this recognition is the further recognition of the increasing importance of analyses of such irregularities.

A known important irregularity is the temporary cessation of breathing during sleep, i.e. a sleep apnea. Three kinds of such sleep apneas are generally recognized in humans, these being central apneas due to problems occurring in the central nervous system, obstructive apneas due to blockages of the air passageways involved in respiration, and mixed apneas involving both of these previous kinds of apneas.

A desirable method of determining the occurrence of obstructive apnea is based on the measurement of volume changes in the human torso due to respiration as an analog of breathing effort changes. This method avoids the need to place something directly into the subject's esophagus to directly measure structural pressure changes, which such a subject will find to be quite uncomfortable during installation and may not tolerate it at all.

There are known methods for monitoring such volume changes along the torso of a subject, including impedance pneumography and inductive plethysmography which are expensive methods and which to some extent pick up unwanted signals such as those accompanying cardiac events. Another known method is the use of a tube about the torso at a selected location having air in the interior space thereof, and a pressure monitoring apparatus connected to that space. The volume changes of the torso at the location of the tube lead to air pressure changes in its interior space which are monitored by the pressure monitoring apparatus.

The use of a tube containing air in its interior space and a pressure monitor provides a cheaper means of monitoring volume changes in the subject's torso than does the equipment used in the first two methods mentioned above. However, there are also difficulties with the use of such a tube-based system which must be overcome. The tube used must not be pinched closed by the weight of the torso of the subject against the tube and the support for the subject and the tube to assure that pressure changes in the tube interior, corresponding to volume changes in the subject's torso due to respiration, are communicated to the pressure gauge. One means of providing that assurance is to inflate the tube with sufficient pressure in the interior thereof so that it cannot be pinched off by the weight of the subject. However, this pressure makes the tube uncomfortable for the subject to wear.

Another means is to have a pair of resilient material strips, or tapes, provided within the tube with a space therebetween so that a passageway is maintained by the material even though compressed by the weight of the subject's torso. However, a satisfactory tube must have walls that are rather thin so that the tube remains sensitive to even small volume changes of the torso of the subject for reasons to be described below. As a result, the tube wall material must be subject to being rather easily deformed. In these circumstances, the tossing and turning of a subject during sleep with such a tube thereabout raises a concern that the two strip portions, joined by portions of the thin wall of the tube, may be repeatedly rolled over one another into a fairly tight twist.

As the result of such twisting, respiration volume changes, reflected by corresponding pressure changes in portions of the tube on one side of such a twist, may no longer be communicated to the other side of the twist which may be the side connected to the pressure monitoring apparatus. Thus, there is a desire to have a volume change monitoring apparatus based on varying air pressure occurring inside a tube placed about the torso of a subject in response to volume changes in that torso at that location configured to assure that pressure changes occurring in any one part of the tube will be communicated throughout and so to a pressure gauge connected thereto.

SUMMARY OF THE INVENTION

The present invention provides a volume change sensor, for sensing volume changes in a flexible body subject to such volume changes, having an elongated tubular enclosure with a thin, deformable wall about an interior region that has a conduit tube extending therefrom to provide access to this interior region by a pressure monitor, there being an elongated insert material in the interior region that is wider than it is thick at least at some locations and formed from resiliently deformable, open cell foam. An elastic belting means with a pair of opposite sides against one of which said tubular enclosure is positioned is used to wrap the tubular enclosure with the insert therein about a subject's torso to measure the volume changes thereof. Two such volume change sensors can be used about a subject's torso to determine the occurrence of obstructive apneas by noting the phasing of the volume changes sensed by each.

BRIEF DESCRIPTION OF THE DRAWINGS

FIG. 2 shows a view of one side of either one of the monitors of FIG. 1, FIG. 3 shows the opposite side of the monitor of FIG. 2, FIG. 4 shows a cross section view of the monitor of FIG. 2, FIG. 5 shows the cross section view of FIG. 4 but under the weight of the torso of the subject in FIG. 1, and FIGS. 6A and 6B show results of monitoring subjects using the present invention.

DETAILED DESCRIPTION OF THE PREFERRED EMBODIMENT

Figure 1:
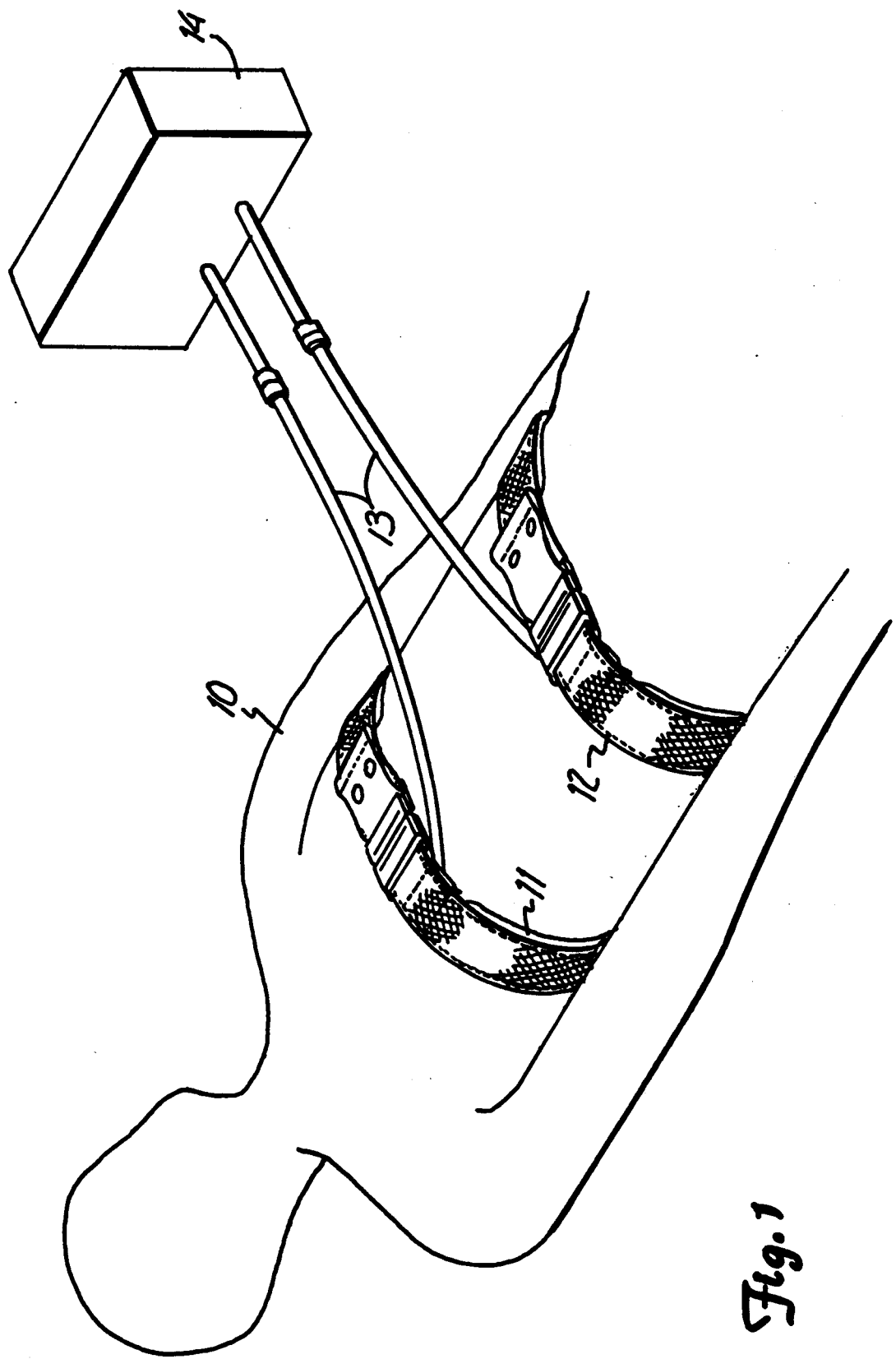
FIG. 1 shows a subject about whose torso a pair of monitors embodying the present invention are positioned at selected locations.

FIG. 1 shows a subject, 10, having a pair of torso volume change monitoring sensors, and 12, positioned about the torso of that subject at a chest location therealong and at an abdominal location therealong, respectively. Sensors 11 and 12 are each connected by a hollow pressure communication tube, 13, to a pressure monitoring apparatus, 14, containing a pressure sensor which is effectively sealed to tube 13 and which can sense pressure changes occurring in the hollow thereof. One reason that sensors 11 and 12 are desired to be sensitive is to permit subject 10 to have some sort of garment on between the torso and either or both of these sensors without resulting in an unacceptable pressure signal from tube 13.

FIG. 2 shows the view of the inside of either of sensors 11 or 12 of FIG. 1, that is, the side of either of sensors 11 or 12 which is facing the torso of subject 10 of that figure. A slight portion of an airtight enclosure, 15, is shown exposed in FIG. 2 with the remaining portions thereof being shown in dashed lines in that figure on both sides of the break therein. That break is provided so that both ends of a sensor 11 or 12 can be shown in the figure which requires a substantial portion of the middle of such sensor to be omitted from being shown there. Airtight enclosure 15 is typically formed of 1.5 inches (3.8 cm) wide (if flattened) polyethylene tubing having a wall thickness of 2.0 mils (0.005 cm). The interior of enclosure 15 is provided with an access to pressure monitoring apparatus 14 by hollow pressure connection tube 13 which has the wall about its hollow passageway connected to the wall of enclosure 15 in an airtight connection. Pressure communication tube 13 is typically formed of flexible polyvinyl chloride tubing having its interior hollow passageway with a diameter of 0.125 inches (0.32 cm), and a passageway wall thickness of 0.125 inches (0.32 cm).

The primary structural member of monitors 11 and 12 to which airtight enclosure 15 is attached is formed by an elastic belt, 16, which can be stretched lengthwise and which, upon release after stretching, returns to approximately its original length. At either end of belt 16 there is provided a corresponding one of two parts of a buckle, 17 and 18 (although for pediatric subjects a "snap-together" means may alternatively be substituted). Elastic belt 16 is formed by a strong but elastic material 2.0 inches (5.1 cm) wide.

The back of belt 16 can be seen in FIG. 3 where portions on either side of the break described in connection with FIG. 2 have been separated into two levels. A series of pairs of snap sockets, 19, are shown along upper level portion of belt 16 in FIG. 3 at the one end thereof, and a pair of snap studs, 20, can also be seen which are inserted into a pair of unseen snap sockets. Snap sockets 19 and snap studs 20 permit a greater or lesser amount of the elastic material in belt 16 to be drawn through buckle piece 17 so as to provide an adjustable length for belt 16 between buckle pieces 17 and 18.

Airtight enclosure 15 is shown attached to the inside of belt 16 in FIG. 2 by a fabric sheathing, 21. Fabric sheathing 21 is a "stretch" fabric having a weave that permits it to be stretched lengthwise to a significant extent, but with very little or no stretching in the direction of its width. Fabric sheathing 21 is stitched to elastic belt 16 at the edges of each so as to form a pocket into which airtight enclosure 15 can be inserted and thereafter remain at a desired positioned along the length of belt 16 between its upper and lower edges in FIG. 2. A strap, 22, is wrapped about pressure change communication tube 13 and held by an unseen snap socket and snap stud, 23, so that airtight enclosure 15 cannot move very far out of the pocket formed between elastic belt 16 and fabric sheathing 21 into which it has been previously inserted.

FIG. 4 shows a cross section view of the sensor of FIG. 2, and reveals that the interior of airtight enclosure 15 contains a resilient material insert, 24, shown as a single entity that essentially fills the cross section of the interior of enclosure 15 at the location of the cross section view. Alternatively, there could be more than one such insert placed more or less end to end with one another. A further alternative would be to fill the interior of enclosure 15 with numerous chunks or balls of the resilient material.

Resilient material 24 is formed of an open cell polyurethane foam of a light to medium density. The open cell nature of this foam allows air flow through the material of insert 24. Thus, even though the wall of airtight enclosure 15 is essentially in contact all around with insert 24, or nearly so, pressure changes occurring in one location along enclosure 15 will be communicated to other parts of enclosure 15 through insert 24 at least.

As the portion of insert 24 at the cross section shown in FIG. 4 comes under pressure due to the weight of the torso of subject 10 against it and the support on which it rests, insert 24 will tend to deform and become thinner as the open cells therein are forced closer together. This closing of the previously open cells at a location in insert 24 will tend to reduce the air flow there through the material of insert 24 which could result in pressure changes in the air within airtight enclosure 15 on one side of the squeezed part of insert material 24 not being communicated to the other side which in some situations will mean also not communicated to tube 13.

However, as can be seen in FIG. 5, which shows the result of the weight of the torso of subject 10 being applied at the location of the cross section view in FIG. 4, the effect of compressing insert 24 from nearly filling the cross section of enclosure 15, as in FIG. 4, to the situation in FIG. 5 is to reduce the fraction of the interior taken up by insert 24 as well as to close its cells to a significant degree. As a result, spaces form within the interior of enclosure 15 between the walls thereof and compress insert material 24 thereby providing an airflow passageway so that pressure changes occurring in one part of enclosure 15 are communicated to the remaining part on the other side of the squeezed portion despite the presence of the weight of the torso of subject 10.

That is, there is a trade-off between the fraction of the interior of enclosure 15 filled by insert 24 and the degree of reduction of the open cells in that insert material. The greater the compression and reduction of the openness of the cells in the material of insert 24 under the weight of subject 10, the greater the amount of interior of enclosure 15 which is no longer occupied by insert material 24.

The choosing of insert material 24 to have a cross section with a substantially longer dimension more or less parallel to elastic belt 16 compared to its dimension more or less perpendicular to belt 16 tends to assure that the added passageways occurring in the interior of enclosure 15 under compression of insert 24 are actually available for communicating pressure changes in the air therein. The freed wall material of enclosure 24 is not merely wrinkled, with parts thereof folded over one another, and then pinched together against the surface of insert 24 under compression to result in closing off part of what should be a passageway. Further, this longer dimension of insert 24 parallel to belt 16 prevents twisting of portions of the monitor when subject 10 slides along the surface of the bed in which the monitoring is occurring, or rolls over in that bed, or performs other such motions. The alternative use of numerous chunks or balls of resilient material can fill airtight enclosure 15 so that a similar cross section results by proper filling of that enclosure with those chunks or balls.

Belt 16 is chosen to be elastic so that when it is positioned around the torso of subject 10 and buckled using buckle portions 17 and 18, it will be slightly stretched so as to provide a net inward force. This net inward force will somewhat compress enclosure 15 and insert 24, and will place the air contained in the interior of enclosure 15 and the interior of tube 13 under some pressure beyond atmospheric pressure. Tube 13 can be initially connected to pressure monitoring aperture 14, or initially unconnected, but before use is to be connected in an airtight connection with that pressure monitoring apparatus. As a result, pressure monitoring apparatus 14 will be able to receive pressure changes both above and below this compressed value (or bias pressure value) rather than being limited on the low pressure side by atmospheric pressure, and so will be able to monitor both increases in torso volume due to inhalations and decreases in torso volume due to exhalations at those locations beneath volume change sensors 11 and 12 on the torso of subject 10.

The use of open cell foam for resilient material 24 can avoid the need in some situations of having to follow an ordered set of steps in positioning the sensors properly about the subject's torso. If the cells could not hold air, the airtight enclosure may have to be sealed to the pressure monitor before being placed about the subject since otherwise the tossing and turning, or other motions, of the subject may rather completely deflate the enclosure before such sealing. This could lead to inconvenient correction procedures or the inability to fully sense torso volume changes. Since open cell foam can hold and pass air, such problems are avoided in the sensor of the present invention even if the sensor is not sealed to the pressure monitor beforehand.

The ability to check both volume increases and decreases at two locations on the torso of subject 10 is important in determining the occurrence of obstructive sleep apneas. The chest and abdominal volume changes have one relationship during normal sleep and breathing, but a changed relationship when an obstructive apnea occurs. Use of two sensors, sensors 11 and 12, each quite sensitive to changes in the torso location volume being measured thereby because of a) the thinness, and so easy deformability of the walls of enclosure 15 therein, and because of b) the kind of resiliency provided by the open cell foam material of insert 24, makes these changing relationships in the event of apnea quite evident at pressure monitoring apparatus 14.

FIG. 6A shows three graphs, the upper being the actual airflow measured in the respiratory passageway by a thermistor for purposes of confirmation of the results from monitors 11 and 12. The second graph presents the pressure changes sensed by sensor 11, and the third graph presents the pressure changes sensed by sensor 12. As can be seen in FIG. 6A, there are regular increases and decreases in airflow measured by the thermistor, and in the volume changes sensed by sensors 11 and 12 as changed internal air pressures $\Delta PRESS_{11}$ and $\Delta PRESS_{12}$, respectively, corresponding to the inhalations and the exhalations during respiration by subject 10. Further, the changes sensed by sensors 11 and 12 can be seen to track one another, i.e. be in phase with one another. That is, the high peak values in each sensor signal occur at approximately the same times that high peak values occur in the other as do the low peak values.

However, in FIG. 6B, the graphs are presented for another subject 10 undergoing obstructive sleep apneas. The thermistor measured airflow there can be seen to have a waveform with an amplitude at some locations therein that is rising and falling substantially during normal inhalations and exhalations, but which goes to a very much smaller amplitude at some other locations indicating a lack of air flow through the respiratory passageway. The torso volume changes sensed by sensors 11 and 12 as sensor internal pressures $\Delta PRESS_{11}$ and $\Delta PRESS_{12}$ are shown to be of substantial amplitude and again in phase with one another where the airflow data indicates normal breathing airflow. However, the torso volume change relationships at the chest and abdomen go to small amplitudes and opposite phases with respect to one another where the airflow data indicates there is little breathing due to an obstruction. Even though the amplitudes of the volume changes (or the corresponding pressure changes in enclosures 15) are usually quite small at the occurrence of an obstruction, the sensitivity of sensors 11 and 12 is sufficient to clearly show the opposite phase effect.

Thus, the use of two sensors like sensors 11 and 12 permits the determination of obstructive apneas without the need for actual airflow data. Since actual airflow data can be quite difficult to get in some instances due to the inability to keep a thermistor in the respiratory passageway of the subject, the opportunity of alternately using just sensors 11 and 12 is a great convenience in avoiding repetitions of sleep tests.

Although the present invention has been described with reference to preferred embodiments, workers skilled in the art will recognize that changes may be made in form and detail without departing from the spirit and scope of the invention.

What is claimed is:

1. A first volume change sensor for sensing volume changes in a flexible body subject to such volume changes, said first sensor comprising:

a tubular enclosure formed by a flexible wall about an interior region, said tubular enclosure being airtight except for at least one conduit having a conduit wall about a conduit passsageway therein connected to said flexible wall at an end of said conduit such that said conduit passageway opens to said interior region of said tubular enclosure with said conduit having an opposite end adapted for connection to a pressure monitor, said tubular enclosure being sufficiently elongated so as to be capable of being positioned substantially about a said flexible body, said flexible wall being sufficiently thin so as to be easily deformable;

an elongated insert formed of a unitary body of resiliently deformable, open cell foam and positioned in said interior region of said tubular enclosure; and an elastic belt with a pair of opposite sides against one of which said tubular enclosure is positioned, said belt having fastening means at opposite ends thereof for being selectively joined together to secure said tubular enclosure about a said flexible body between said belt and that said flexible body; said insert, if undeformed by external forces at a cross section thereof taken substantially perpendicular to its direction of elongation, having an extent at that cross section in a direction substantially parallel to said belt exceeding its extent there in a direction substantially perpendicular to said belt; wherein said insert is an entity that, if undeformed, has an area at said cross section thereof that exceeds half that area at its greatest extent of a substantially parallel cross section of said tubular enclosure at that same location.

2. The sensor of claim 1 wherein said cross sectional area of said insert is substantially equal to said cross sectional area of said tubular enclosure.

3. A first volume change sensor for sensing volume changes in a flexible body subject to such volume changes, said first sensor comprising:

a tubular enclosure formed by a flexible wall about an interior region, said tubular enclosure being airtight except for at least one conduit having a conduit wall about a conduit passageway therein connected to said flexible wall at an end of said conduit such that said conduit passageway opens to said interior region of said tubular enclosure with said conduit having an opposite end adapted for connection to a pressure monitor, said tubular enclosure being sufficiently elongated so as to be capable of being positioned substantially about a said flexible body, said flexible wall being sufficiently thin so as to be easily deformable;

an elongated insert formed of resiliently deformable, open cell foam and positioned in said interior region of said tubular enclosure; and an elastic belt with a pair of opposite sides against one of which said tubular enclosure is secured to said elastic belt by a fabric attached to said belt, said belt having fastening means at opposite ends thereof, for being selectively joined together to secure said tubular enclosure about a said flexible body between said belt and that said flexible body; said insert, if undeformed at a cross section thereof taken substantially perpendicular to its direction of elongation, having an extent at that cross section in a direction substantially parallel to said belt exceeding its extent there in a direction substantially perpendicular to said belt, said fabric having a weave which can stretch relatively far substantially parallel to the direction of elongation of said tubular enclosure but can stretch relatively little in a direction transverse thereto.

4. A method for determining whether obstructional apneas are occurring in a respirating subject through measurement of volume changes at each of selected regions of that subject undergoing such volume changes because of respiration, said method comprising:

providing a first volume change sensor about said subject's torso at a chest location, and providing a second volume change sensor about said subject's torso at an abdominal location, said first and second volume change sensors each being capable of providing a varying air pressure in a corresponding conduit extending therefrom as a result of corresponding variations in volume of said subject's torso at that sensor's location;

comparing over time air pressure changes from said first and second volume change sensor conduits; and selecting at least some of those occasions in which air pressure in said first volume change sensor is increasing and said air pressure in said second volume change sensor is decreasing, and vice versa, as indications of obstructive apneas.

5. A first volume change sensor for sensing volume changes in a flexible body subject to such volume changes, said first sensor comprising:

a tubular enclosure formed by a flexible wall about an interior region, said tubular enclosure being airtight except for at least one conduit having a conduit wall about a conduit passageway therein connected to said flexible wall at an end of said conduit such that said conduit passageway opens to said interior region of said tubular enclosure with said conduit having an opposite end adapted for connection to a pressure monitor, said tubular enclosure being sufficiently elongated so as to be capable of being positioned substantially about a said flexible body, said flexible wall being sufficiently thin so as to be easily deformable;

an elongated insert formed of a plurality of resiliently deformable, open cell foam pieces each abutting at least one other and positioned in said interior region of said tubular enclosure; and an elastic belt with a pair of opposite sides against one of which said tubular enclosure is positioned, said belt having fastening means at opposite ends thereof for being selectively joined together to secure said tubular enclosure about a said flexible body between said belt and that said flexible body; said insert, if undeformed by external forces at a cross section thereof taken substantially perpendicular to its direction of elongation, having an aggregate extent at that cross section in a direction substantially parallel to said belt exceeding its extent there in a direction substantially perpendicular to said belt.

6. The sensor of claim 5 wherein said insert is an entity that, if undeformed, has an area at said cross section thereof that exceeds half that area at its greatest extent of a substantially parallel cross section of said tubular enclosure at that same location.

7. The sensor of claim 6 wherein said cross sectional area of said insert is substantially equal to said cross sectional area of said tubular enclosure.

* * * * *

UNITED STATES PATENT AND TRADEMARK OFFICE
CERTIFICATE OF CORRECTION

PATENT NO. : 5,191,893
DATED : March 9, 1993
INVENTOR(S) : DENISE M. REITEN

It is certified that error appears in the above-identified patent and that said Letters Patent is hereby corrected as shown below:

On title page, item [56] under U.S. PATENT DOCUMENTS, delete "4,813,429  3/1989  Muraki et al.....128/736"
   insert --4,813,428  3/1989  Muraki et al....128/736--

Col. 7, line 39, after "thereof", delete -- , --

Signed and Sealed this

Eighth Day of February, 1994

Attest:

BRUCE LEHMAN

Attesting Officer

Commissioner of Patents and Trademarks